Nov. 19, 1963 H. B. LEWIS ETAL Plant Pat. 2,309
AZALEA PLANT
Filed Sept. 28, 1962 2 Sheets-Sheet 1
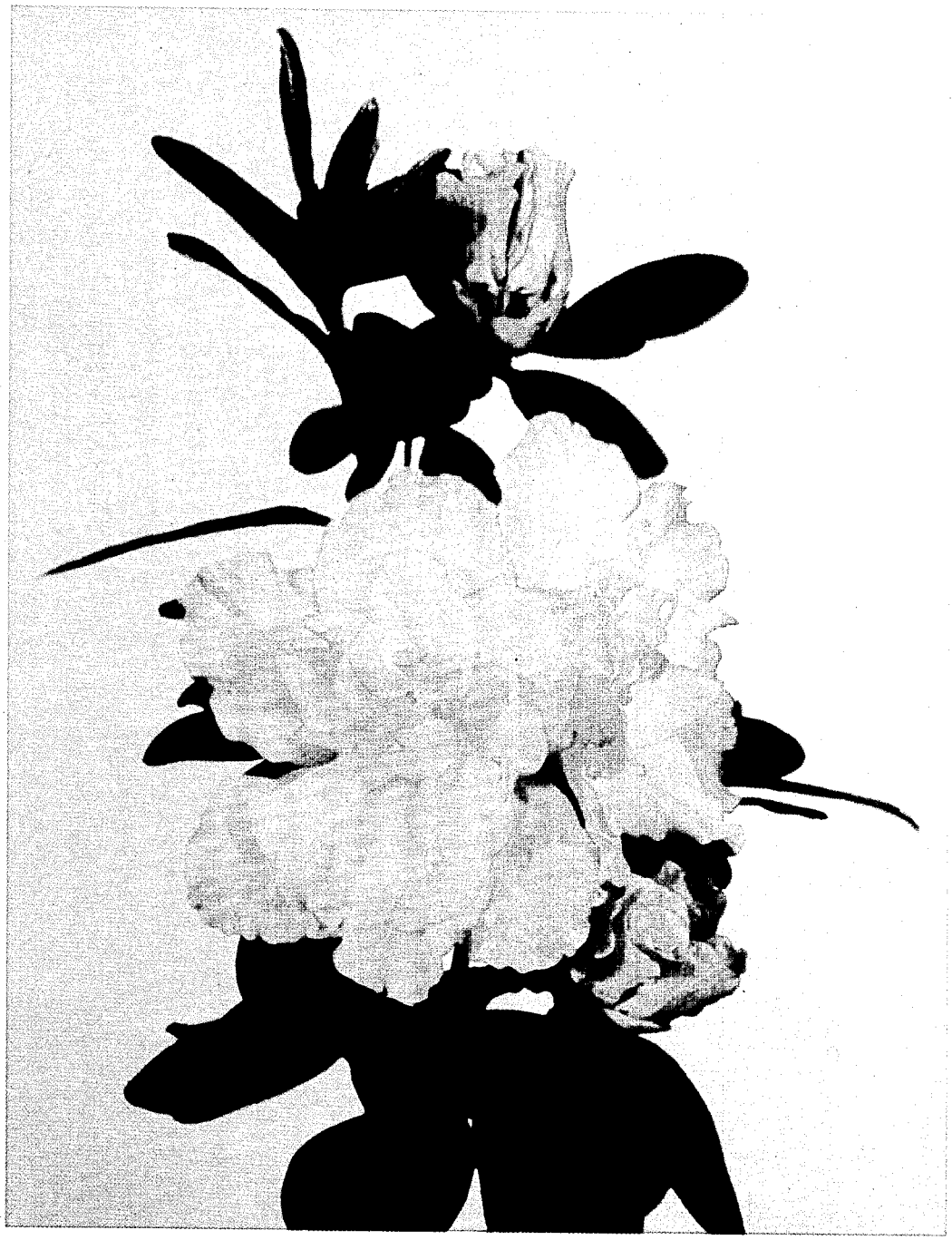
Inventors.
H. B. Lewis and
H. H. Lewis
By: Robb & Robb
Attorneys.

Nov. 19, 1963 H. B. LEWIS ETAL Plant Pat. 2,309
AZALEA PLANT
Filed Sept. 28, 1962 2 Sheets-Sheet 2
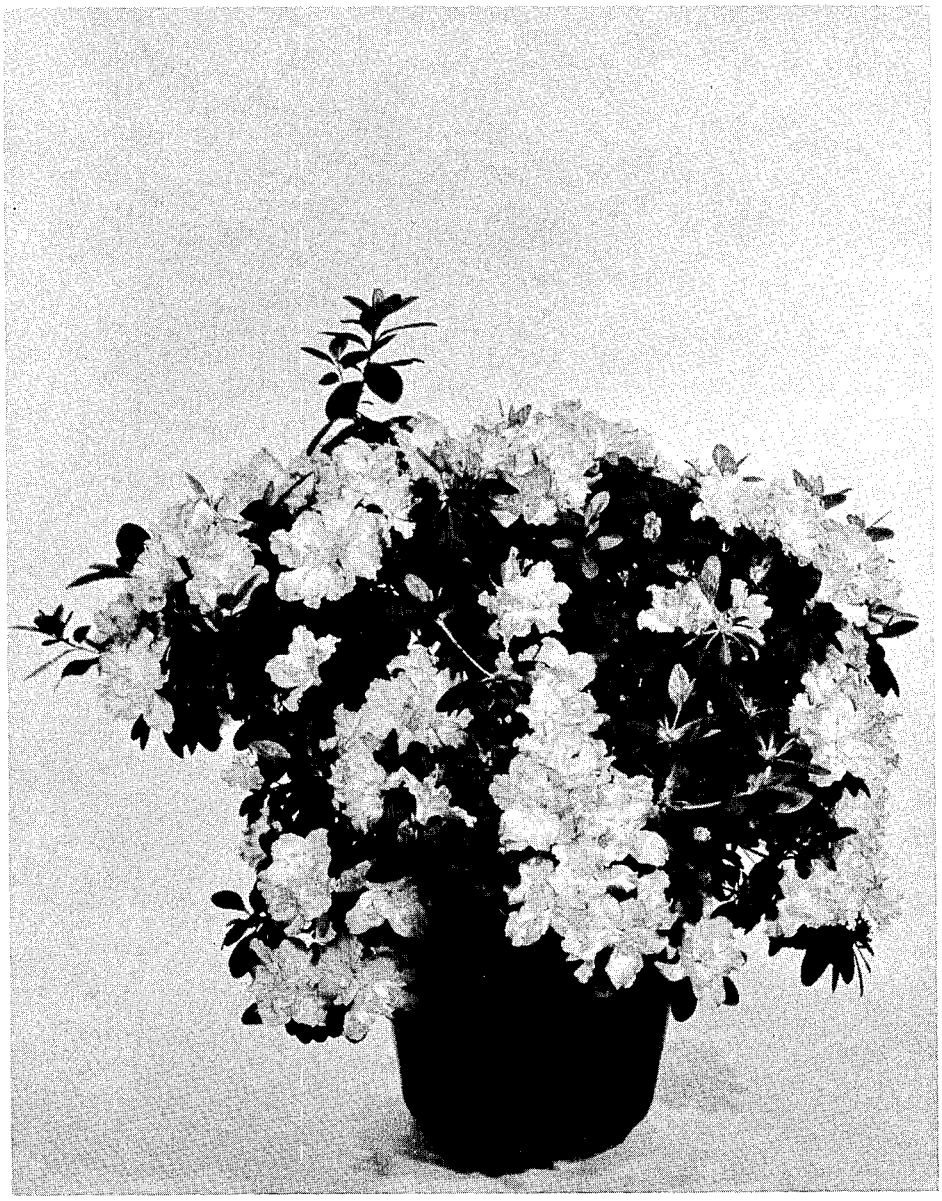
Inventors.
H. B. Lewis and
H. H. Lewis
By: Robb & Robb
Attorneys.

United States Patent Office

Plant Pat. 2,309
Patented Nov. 19, 1963

2,309
AZALEA PLANT

Hubert B. Lewis and Helen H. Lewis, both of 16562 E. Leffingwell Road, Whittier, Calif.

Filed Sept. 28, 1962, Ser. No. 227,097
1 Claim. (Cl. Plt.—55)

The present invention relates to a new and distinct variety of azalea plant which was originated by us by crossing the Belgian Indian variety known as "Brillanta Belgica" (unpatented) with the variety known as "Mme. Pericat" (unpatented), the former being the seed parent and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varieties of which we are aware:

(1) Large size, strong and fast-growing habits of growth;

(2) Foliage of medium size and good quality;

(3) A distinctive, attractive and unusual pink general color tonality of the flowers, with the pink color being darker on the outer edges of the petals and shading to almost white at the center of the flowers, thereby giving the flowers an appearance of being "frosted" with pink; and (4) Suitability for forcing.

Our new variety does not resemble either parent in any way. It has better foliage than either parent, and the flowers differ in color from those of most all other varieties of which we are aware and have a very unusual frosted appearance.

Asexual reproduction of our new variety by cuttings, as performed at Rivera, California, and at Whittier, California, shows that the foregoing characteristics and distinctions come true to form and are established and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

The following is a detailed description of our new azalea variety, with color terminology in accordance with the Wilson Horticultural Color Chart, except where general color terms of ordinary dictionary significance are obvious:

Locality where grown and observed: Whittier, California.
Propagation: Holds its distinguishing characteristics through succeeding propagations by cuttings.

*Plant*

Form: Generally upright.
Habit: Vigorous; branching; rather sprawling when not pruned.
Rooting habit: Good.
Foliage:
*Size.*—From medium to large.

*Quantity.*—Normal.
*Color.*—New foliage: upper side—Spinach Green, Plate 0960/2; under side—Scheeles Green, Plate 860. Old foliage: upper side—Parsley Green, Plate 00962; under side—Spinach Green, Plate 0960/3.
*Texture.*—Smooth on both upper and under sides.
*Margin.*—Smooth.
*Aspect.*—Smooth.
*Disease resistance.*—Good resistance to ordinary diseases to which azalea plants are normally subject, as determined by comparison with other varieties grown under the same cultural conditions at Whittier, California.

*Flowers*

Borne: From 2 to 6 to stem; on strong stems.
Blooming habit: Blooms evenly over entire plant.
Blooming season: Normally in spring, but by pruning, can be forced to bloom from Christmas to Easter season.
Quantity of bloom: Free, both outdoors and in greenhouse.
Continuity: Heavy from Christmas to Easter seasons.
Petalage: Normally 5 outer petals and 5 smaller inner petals.
*Color.*—Very narrow outer border of Phlox Pink, Plate 625, shading to Phlox Pink, Plate 625/1 from edge to center of petals, and then shading to Phlox Pink, Plate 625/3 from center of petals to throat.
*Texture.*—Heavy; crisp.
*Appearance.*—Appears frosted with an overlay of pink color on white.
*Shape.*—Semi-double.
*Arrangement.*—Outer petals—flat. Inner petals—raised.
Bud: Ruffled appearance. Color—Phlox Pink, Plate 621/1.

*Reproductive Organs*

Stamens: 4 or 5 in number; mostly attached to inner petals. Color—from light pink to yellow.
Pollen: Sparse. Color—white.
Styles: Well developed. Color—Yellow in center.
Ovaries: Normal.

We claim:

A new and distinct variety of azalea plant, substantially as herein shown and described, characterized particularly as to novelty by the unique combination of large size, strong and fast-growing habits of growth, foliage of medium size and good quality, a distinctive, attractive and unusual pink general color tonality of the flowers, with the pink color being darker on the outer edges of the flower petals and shading to almost white at the center of the flowers, thereby giving the flowers an appearance of being "frosted" with pink color, and suitability for forcing.

No references cited.